United States Patent [19]

Miller et al.

[11] Patent Number: 5,395,374
[45] Date of Patent: Mar. 7, 1995

[54] ORTHOPEDIC CABLING METHOD AND APPARATUS

[75] Inventors: David F. Miller, Eads; Michael C. Sherman; Robert A. Farris, both of Memphis, all of Tenn.

[73] Assignee: Danek Medical, Inc., Memphis, Tenn.

[21] Appl. No.: 116,130

[22] Filed: Sep. 2, 1993

[51] Int. Cl.⁶ ............................................. A61B 17/56
[52] U.S. Cl. ...................... 606/74; 606/61; 606/86; 606/103; 606/151
[58] Field of Search .......... 606/60, 86, 103, 232, 606/157, 158, 61, 151, 74

[56] References Cited

U.S. PATENT DOCUMENTS

| | | | |
|---|---|---|---|
| 3,111,945 | 11/1963 | Von Solberg | 606/103 |
| 3,507,270 | 4/1970 | Ferrier | 606/103 |
| 4,889,110 | 12/1989 | Galline et al. | |
| 4,996,600 | 10/1990 | Songer et al. | |
| 5,116,340 | 5/1992 | Songer et al. | |

*Primary Examiner*—Tamara L. Graysay
*Attorney, Agent, or Firm*—Woodard, Emhardt, Naughton, Moriarty & McNett

[57] ABSTRACT

A double-apertured L-shaped crimp is crimped to one end of a cable. The other end of the cable is passed around the bone and an orthopedic device to be attached to the bone, and it is then passed through the other aperture in the crimp. A releasable, lever-operated cable clamp is installed on the cable, followed by a tensioning tool. The tensioning tool applies a pre-positioning tension on the cable. The cable clamp is clamped to the cable to hold the tension. The tool is removed for use on another cable. When ready for final tensioning, the tensioning tool is re-installed, adjusted to the desired final tension, the crimp swaged onto the cable to hold the final tension, the cable clamp unclamped, the tensioning tool released and removed with the cable clamp, and the cable is cut off at the crimp.

24 Claims, 6 Drawing Sheets

ORTHOPEDIC CABLING METHOD AND APPARATUS

BACKGROUND OF THE INVENTION

Field of the Invention

This invention relates generally to orthopedics and spinal surgery, and more particularly to a method and apparatus for securing cable to bone.

Description of the Prior Art

Many ways and means have been developed for securing bone in place and for securing devices to bone. While single filament wires were used for many years in various types of surgical procedures, multi-filament cables have been used increasingly in recent years, particularly where strength and long-term reliability in a comparatively inaccessible site, are important. One example is shown in U.S. Pat. No. 4,889,110 issued Dec. 26, 1989 to Galline et al. In that example, an anchoring plate 11 has four bores therein receiving two crimping tubes and two crimping rings for holding multi-ply cables to secure a trochanter major to the femur. Another example of use of multi-filament cables is shown in U.S. Pat. Nos. 5,116,340 and 4,966,600 to Songer et al. The latter patent uses a loop 38 and a flanged tube crimp 28 as in FIG. 1 of Songer, or a stop member 94, bar 96 and a crimp having a front flange 60 as in FIG. 6 of Songer, to secure the cable. Those crimps, because of an appearance somewhat similar to a top hat have been referred to in the profession as "tophat" crimps. Because of the need to minimize space requirements for cabling, crimps of the type shown in the Songer patents are small. As a result, they are difficult to handle, cannot be manipulated well with surgical gloves, and can be dropped easily. Therefore it was desirable to provide a system whereby a separate loose crimp is not needed and the crimp is reliably secured and securable to the cable and which does not require cable-to-cable contact stress as in the cable passing through the small loop 38 in the FIG. 1 embodiment of the Songer patents. Therefore a new, cable-mounted crimp has been invented for that purpose. In addition, regardless of whether a separate loose crimp is used, or the new type of cable mounted crimp is used, it would be desirable to be able to pre-position the crimp in the approximate final position it would have on the cable but, before crimping onto the cable in final position, be able to make some final positioning adjustments of the cable with respect to the bone and to fixation devices used on the bones, particularly during spinal surgery. It would also be desirable to be able to perform this function on several cables during a procedure but without the necessity of having several cable tensioning tools in use at the same time to hold pre-final positioning tension on the cables. In fact, with the tophat crimps, some practitioners correcting spinal deformity conditions, adopted a procedure using at least two tophat crimps per cable. In that case, two crimps were used on each cable at different locations on the spine. When a cable was tightened with the Songer-type tensioner onto a bone and spinal rod, for example, the outboard crimp was crimped onto the cable. The inboard crimp was left uncrimped. This procedure was followed along the spine until all cables were crimped. As the surgeon would proceed from one cable and work on the next cable, it would occasionally occur that the tension in one or more of the first cables which had been tensioned, would decrease due to movement of the rod or bones. Then the surgeon would go back and apply additional tension to those cables and then crimp the inboard crimp onto the cable. Then the cable was cut between the inboard and outboard crimps, and the outboard crimp and cable were discarded. That procedure wasted all of the outboard crimps, all of which were made of implant-grade material. The present invention addresses that problem.

SUMMARY OF THE INVENTION

Described briefly, according to a typical embodiment of the present invention, a double-apertured crimp has one apertured portion crimped or otherwise fixed to one end of a cable. The other end of the cable is passed around the bone or bones and any orthopedic appliance or fixation device to be attached by the cable to the bones, and the cable is then passed through the other aperture in the crimp. The cable is then passed through a small lever-action cable clamp. The cable is then tensioned by application thereto of a tensioning tool, with the tool applied to the cable and to an abutment face in a socket in one end of the cable clamp. An abutment face at the other end of the cable clamp is applied to an abutment face of the crimp. Thus the cable clamp is located between the crimp and the tensioning tool. Then the cable is tensioned to a pre-final amount suitable for holding things in place while adjustments are made in the positioning of the cable and any fixation devices connected to the cable, relative to the bones. Then the lever on the cable clamp is operated to secure the clamp on the cable, thereby maintaining the tension on the cable so that the tensioning tool can be removed from the cable and used on another cable used in the procedure. After the surgeon determines that the cable is properly positioned, the tensioning tool is again installed on the cable and engaged with the cable clamp and set to the previously set, pre-final tension in the cable. Then the lever on the cable clamp is released, and the tensioning tool is adjusted to increase or (and less likely) decrease the tension to the desired final amount for the permanent position of the cable. Then the crimp is crimped onto the cable. Then the tensioning tool is removed, the cable clamp removed and the loose end of the cable is trimmed off at the abutment face of the crimp.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
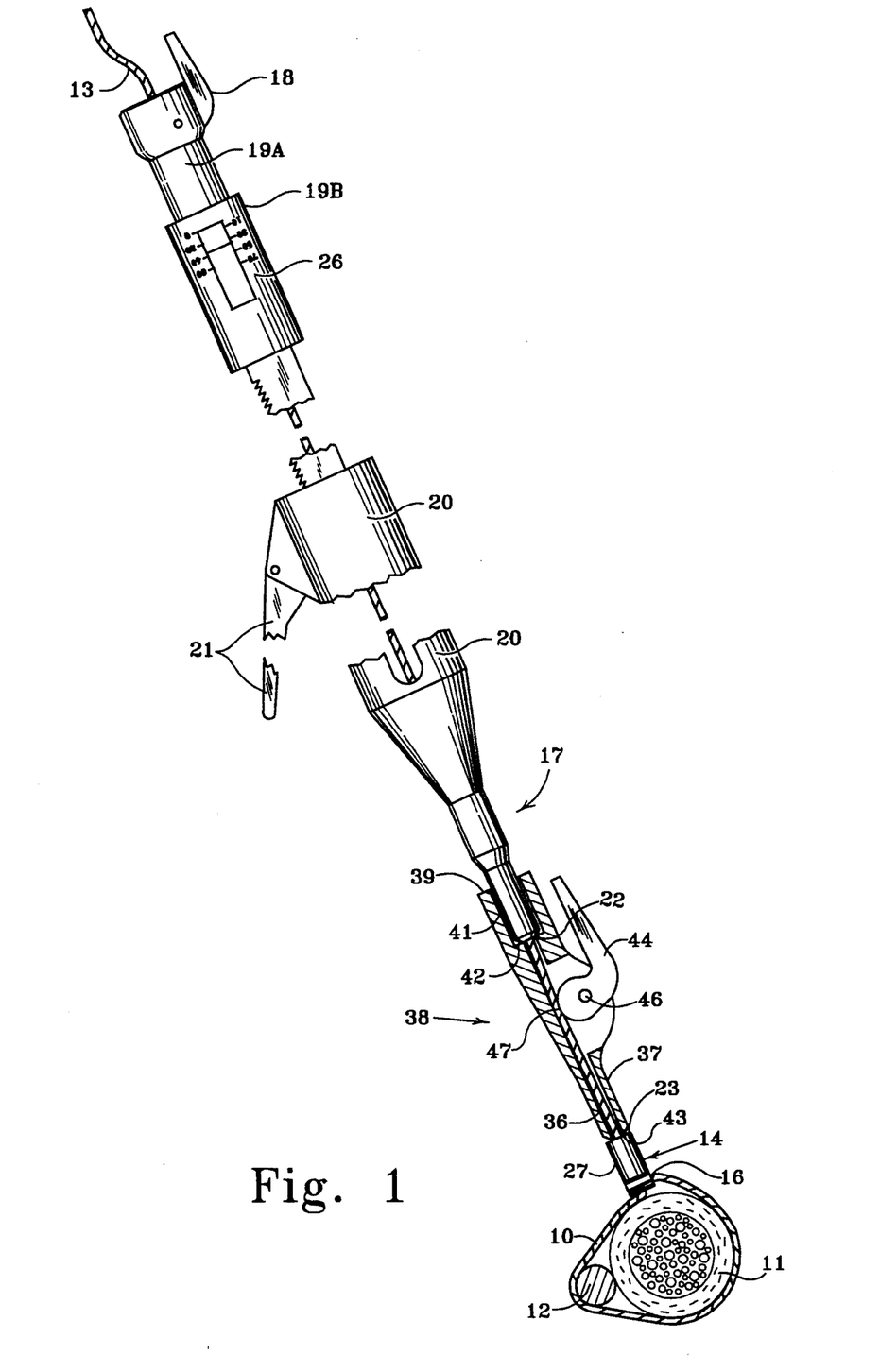
FIG. 1 is a schematic illustration of the application of the crimp assembly to a bone and rod using the method and apparatus of the present invention.

Referring now to the drawings in detail, and more particularly FIG. 1, the goal is to secure cable 10 around bone 11 and rod 12 with the proper tension on the cable, and maintain it. For that purpose, the free end 13 of the cable is passed around the bone 11 and rod 12 while the crimp 14 which was factory-fixed at the other end 16 of the cable (FIG. 2), is held at a suitable location above the bone. Then the cable free end 13 is passed up through an aperture 24 in the crimp and then through the central passageway in a tensioning tool 17. However, according to the present invention, before inserting the free end of the cable into the tensioning tool, it is inserted into the axially extending passageway 36 in the small tip portion 37 of a cable clamp 38, and the cable is passed up through passageway 36 and out the upper end 39 of the clamp. Then the cable free end 13 is passed up through the central passageway in the tensioning tool 17. Then the tensioning tool is slid down the cable, and tip 22 of its barrel tip portion is inserted into the cylindrical tool-receiving socket 41 at the upper end of the clamp 38 and advanced until the flat end of tip 22 abuttingly engages the tool receiving abutment wall 42 at the bottom of the socket inside the clamp 38. The small flat tip end 43 of the cable clamp 38 abuttingly engages the tool-receiving flat upper end 23 of the crimp 14.

Figure 3:
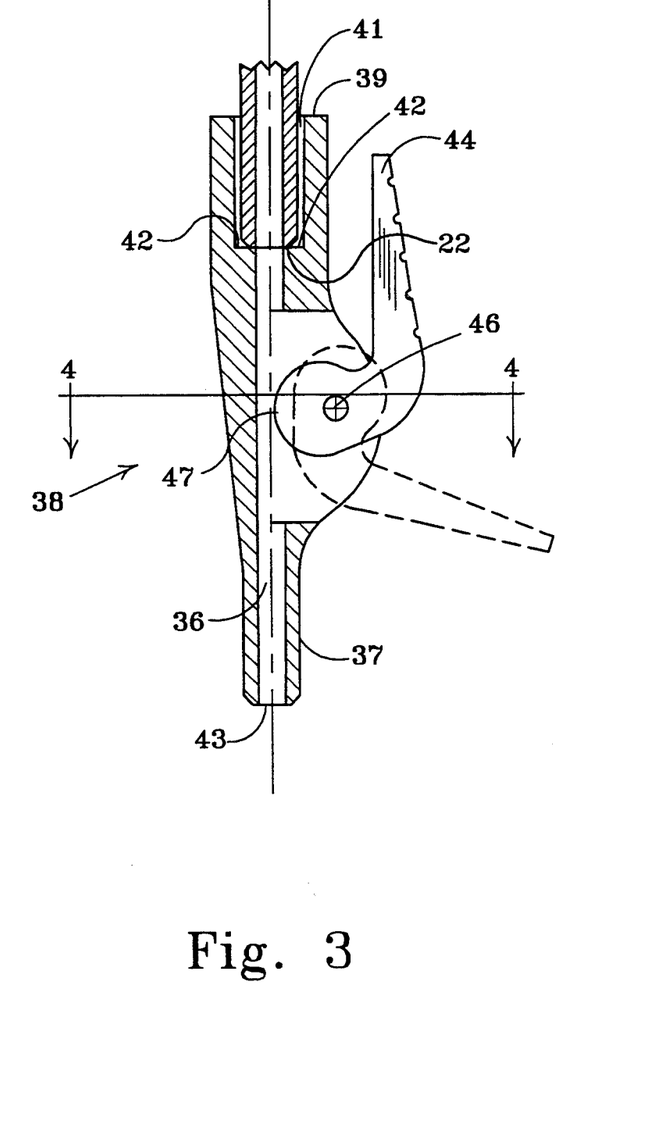
FIG. 3 is an enlarged longitudinal sectional view of the cable clamp installed on the end of the tensioner (shown fragmentarily).

While the cable and the tensioning tool are held so that the tool-to-clamp and clamp-to-crimp surfaces remain in contact, a clamp cam operating lever 18 at the upper end of the tensioning tool is operated to the solid line position shown in FIG. 1 and clamps a portion 19A of the tensioning tool onto the cable. Portion 19A telescopes within portion 19B which is secured to a bar which telescopes into the barrel 20 of the tensioning tool. Upon operation of the hand lever 21, portion 19B is ratcheted out of the barrel 20. The barrel tip 22 abuttingly engages and bears on the tool receiving abutment wall 42 inside the clamp 38, and the clamp tip 43 abuttingly engages and bears on the upper end 23 of the crimp member. Further ratcheting of the tool pulls the cable up through the aperture 24 in the crimp 14 and aperture 36 in the clamp 38 until a tension is reached which is sufficient to hold the rod 12 in place against the bone, but possibly with less than the final tension to be applied when the rod and any other fixation devices associated with the rod are in the desired final position with respect to the bones. The amount of this pre-final tension is indicated on the scale 26 on portion 19B in which portion 19A is restrained by a calibrated spring. Note is made of the amount of tension, for further reference. Then the lever 44 which is rotatable on shaft 46 in cable clamp 38 from the open (dotted line) position in FIG. 3, is pushed down to the closed solid line position in FIG. 1, causing the cam portion 47 thereof to grip the cable tight. Then, lever 18 of the tensioning tool can be opened and the tool removed from the cable. The cable clamp will maintaining set tension in the cable. Then the tensioning tool can be moved to and operated on another cable and clamp in the same way. In this way, several cables and associated fixation devices can be positioned and held with the tension needed for working with and positioning them before final tensioning. This is particularly desirable where multiple cables are being used at spaced locations along a rod or other fixation device.

Figure 5:
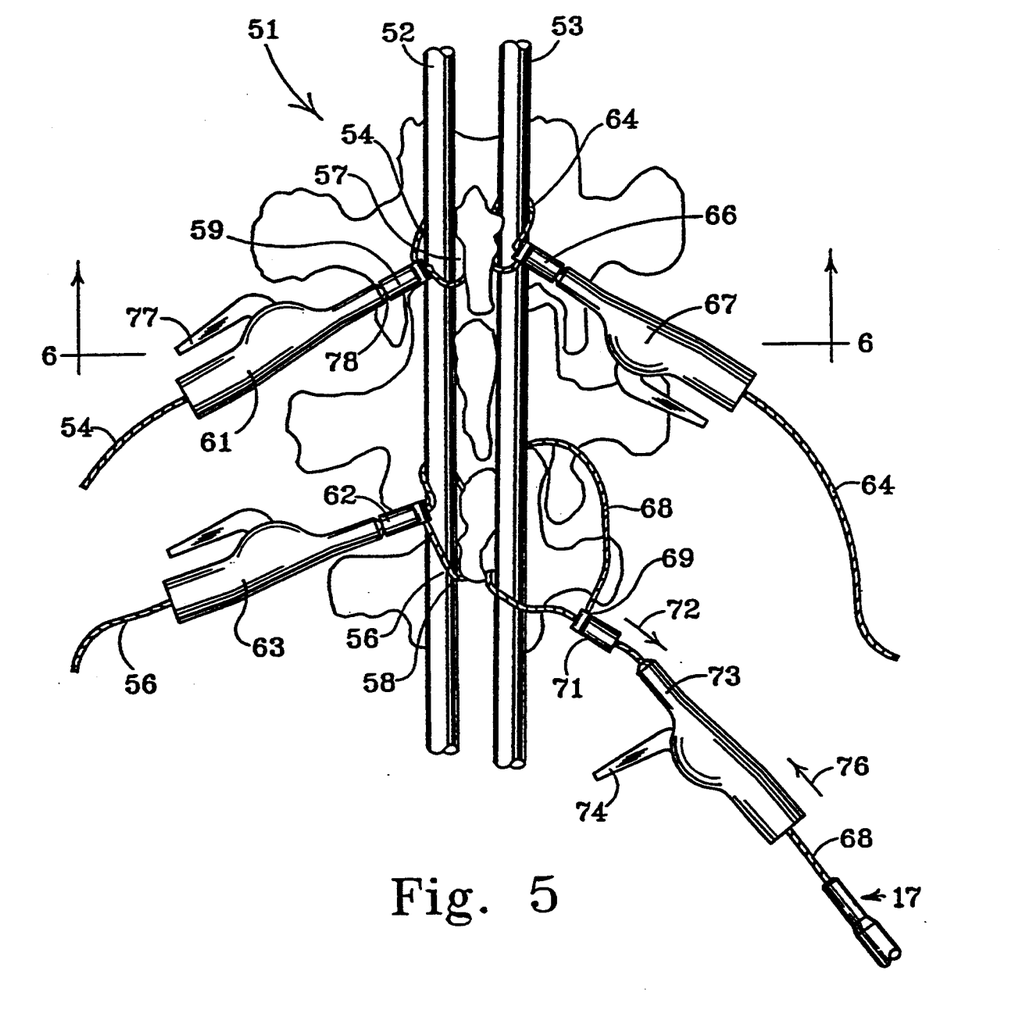
FIG. 5 is a schematic diagram of a portion of a spinal column showing several cables holding implants thereon according to a typical embodiment of the present invention.

Referring now to FIG. 5, there is shown fragmentarily a portion of spinal column 51 to which two spinal rods 52 and 53 are being secured by cables as can be done to correct a spinal deformity such as scoliosis, for example. Cables 54 and 56 are being used to secure the rod 52 to bones 57 and 58 in the spinal column. Cable 54 has been tightened around bone 57 and rod 52 and the free end of it has been passed through the aperture in the crimp 59 and cable clamp 61 and extends out of the cable clamp. Although the cable is broken off in the drawing to conserve space, it should be understood that sufficient cable extends out of the cable clamp to easily enable re-installation of the tensioning tool 17 thereon for re-tensioning the cable if needed. Similarly, cable 56 extends through the crimp 62 and clamp 63 which is abuttingly engaged with the crimp, and out the opposite end of the clamp 63.

The other spinal rod 53 is fastened to bone 57 by cable 64 which extends through the crimp 66, clamp 67 and out of the clamp. This clamp is holding tension on the cable 64 securing the rod 53 and bone together. Cable 68 is about to be secured to bone 58 and rod 53, the one end 69 of cable 68 being fixed in the crimp 71, and the other end of the cable having been threaded through the other aperture in the crimp in the direction of arrow 72 and through the axial passageway in the center of the cable clamp 73 and through the tip portion of the tensioning tool 17 (shown only fragmentarily to conserve space). The lever 74 of the clamp 73 is open so that the clamp can freely slide along the cable in the direction of arrow 76. The cable 68 is pulled tight, bringing the crimp 71 snug up against the rod 53. Then the clamp 73 is pushed up against the end of the crimp 71, and the tip portion of the tensioning tool 17 is pushed into the socket in the cable clamp whereupon all of the parts 71, 73 and 37 are pushed together. Then the clamp lever 18 on the tensioner tool (FIG. 1) is closed onto the cable and the ratchet handle 21 is operated to pull that cable tight around the bone and rod 53. This is the same procedure as has been followed with respect to the other cables 54, 56 and 64 which are already tensioned around the bones and respective rods.

After the cable 68 is properly tensioned and the clamp 73 secured to the cable, the same procedure can be followed for additional cables and bones along the rods 52 and 53. After this procedure has been completed, and if any of the previously secured cables such as 54 or 64 or 56 or 68 are no longer quite as tight as they should be due to some relaxation of tension as the spine is straightened during the procedure, the tensioner can again be installed on any of the cables 54, 56, 64 or 68 or others, if needed, to tighten them to the correct final tension. When that has been accomplished on cable 54, for example, a crimping tool is applied to the crimp 59 to crimp it permanently onto the cable and hold the desired tension in cable 54. Before the final tightening of cable 54 is done, the tensioning tool can be operated to tension the cable sufficiently between the tool and the clamp 61 to avoid abrupt movement of the cable when lever 77 of the clamp is opened to release the clamping cam from the cable. In fact, the cam is designed to be self-locking in one direction so that, when the lever is closed, the cam will not permit movement of the cable relative to the clamp in the direction of arrow 76, but the cable can be pulled through it by the tensioning tool in the direction of arrow 72. Therefore, it is not necessary to manually open lever 77 for final tightening of the cable. When the desired final tension has been established in the cable, the crimp 59 is crimped permanently onto the cable. If the lever 77 hasn't been opened already, it can now be opened, whereupon the tensioning tool can be released and removed from the cable and the clamp 61 can be removed from the cable. Then the cable is cut off at the outboard end 78 of the crimp 59. The same procedure can be followed with respect to the other cables.

Figure 4:
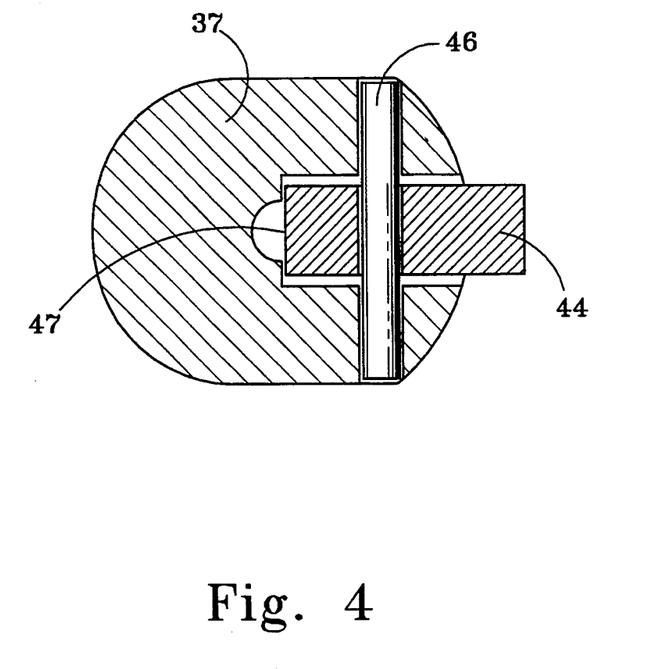
FIG. 4 is a cross sectional view of the cable clamp taken at line 4—4 in FIG. 3 and viewed in the direction of the arrows.

To be more specific regarding the re-visiting of a cable such as 54 in FIG. 4 or cable 10 in FIG. 1, for example, when the surgeon is satisfied that the rod and/or other parts and the cable are properly positioned for final tensioning or, upon noting that the tension in this cable has dropped from previously established desired tension during work at other locations along the rod, the tensioning tool can be installed on the cable again as before. With the tip 22 securely seated at the bottom of the socket, the lever 18 on the tensioning tool is closed onto the cable. The ratchet is operated until the previously established pre-final tension reading appears on the scale or the surgeon is otherwise satisfied that the tension has been increased to the desired final level by operating the ratchet handle 21. Then a separate crimping tool (not shown) is applied to the portion 27 of the crimp 14 (FIG. 1) and crimps it onto the cable portion extending through aperture 24 thereby fixing the cable in the aperture and holding the final tension in the cable around the bone. Then the tool clamp lever 18 can be loosened, and the cable clamp lever 77 opened (if not previously opened) whereupon the tensioning tool and cable clamp 38 can be removed from the cable. Then the cable is cut off at the crimp abutment face 23, flush with face 23. The cable remains secured to the bone and rod.

Figure 2:
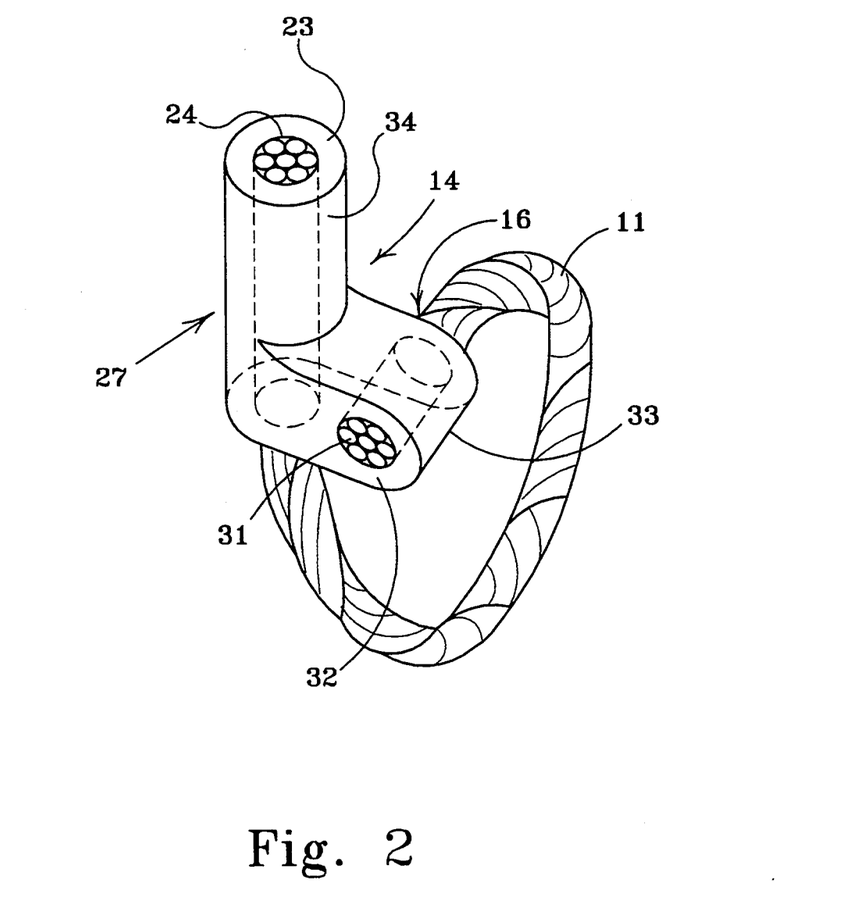
FIG. 2 is an enlarged fragmentary view of the crimp assembly as looped but with the bone and rod omitted.

Referring to FIG. 2, the one end 31 of the cable portion received in the base portion 32 of the crimp 14, has been secured therein by swaging at 33 in a die press at the factory. After the cable has been wrapped around the bone and rod and adequately tensioned to the final amount of tension during surgery, as described above, the column portion 27 is swaged as at 34 by a suitable crimping tool such as are known in the art. The cable end received up through the longitudinal aperture 24 from the bottom 36 to the top abutment surface 23 is cold crimped by such a tool after the desired final tension has been applied to the cable.

Figure 6:
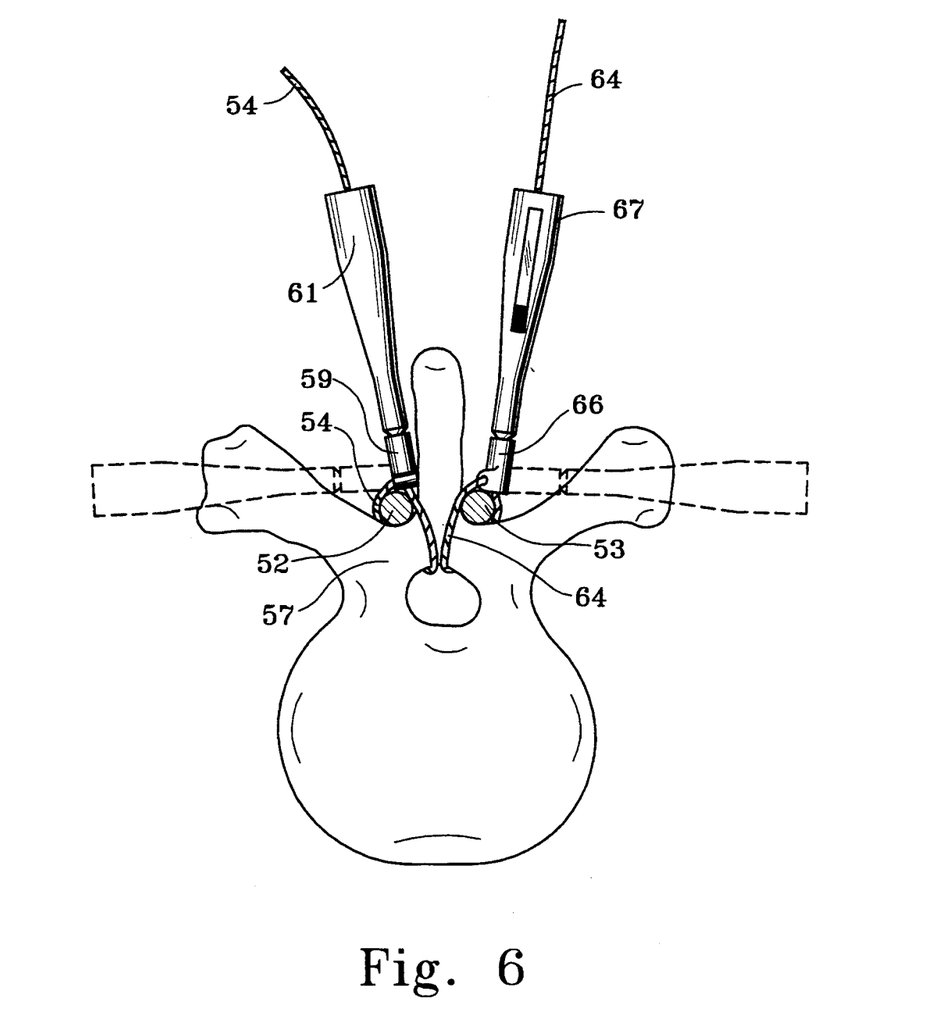
FIG. 6 is a cross section taken at line 6—6 in FIG. 5 and viewed in the direction of the arrows, but showing a different orientation of the cable clamps.

Referring to FIG. 6, another feature of the present invention is illustrated. When the cables are sufficiently tensioned, and the tensioning tool is removed, the cable clamps will stand up in the wound in the patient's back substantially as shown in FIG. 6. As additional cables are installed and tightened during a procedure to correct an abnormal spine condition, the movement of bones may result in some of the previously tensioned cables becoming less tight. When that occurs, the weight of the cable clamp will overcome the tendency of a previously tight cable to hold the clamp erect, and the clamps will begin to lie down in the wound toward the generally horizontal positions shown by the solid lines in FIG. 5 (the broken lines in FIG. 6). The surgeon is thereby provided with a quick and convenient indicator of which cables definitely need to be re-visited for re-tensioning.

As an example, and to minimize the space requirement of the cable clamp, the diameter of the tip portion 37 of the cable clamp is 0.240 inches, the same as that of the barrel tip portion of the tensioner. The socket internal diameter is about 0.260 inches, and its depth is about 0.450 inches. The overall length is about 1.500 inches. The material is 17-4 PH cast stainless steel. The cam and lever member is made of 455 stainless steel. The center of the cam curve is offset from the axis of camshaft 46 for progressive tightening of the cam on the cable as the lever is initially closed from the dotted line position, but slight release as it approaches the closed solid line position, whereby the clamp is self-locking in one direction to prevent the clamp from backing out along the cable in the direction of arrow 72.

It should be understood, of course, that if it is desired to secure two bones within the loop of the cable, or one or more bones and one or more spinal rods or other fixation devices within the loop, or two or more cables in series and then around the bone and implant, that can be done in a similar manner. The present invention can be used not only with the type of cable end stop shown in the drawings herein, but also with the types of stops (loops, crimps, or bars, for example) shown in the above-mentioned Galline and Songer patents.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for securing cable around bone and comprising the steps of:
   taking a cable having one end with a stop thereon, and passing the other end of the cable around the bone and returning toward the stop;
   feeding the other end of the cable through an aperture in the stop;
   feeding the other end of the cable through an aperture in a manually closable and releasable cable clamp and resting the clamp on the stop;
   engaging a cable tensioning tool with the clamp and with a portion of the cable between the clamp and the other end of the cable after the other end was fed through the aperture in the clamp;
   using the tool for applying positioning tension on the cable;
   temporarily fixing in the clamp aperture, that portion of the cable residing in the clamp aperture when the applied tension on the cable is at a desired positioning value; and
   removing the tensioning tool from the cable.

2. The method of claim 1 and wherein:
   the fixing step is performed by moving a lever on the clamp and thereby forcing a cam surface of the clamp into clamping relationship on the cable portion residing in the clamp aperture.

3. The method of claim 1 and wherein:

the steps of passing and feeding and tensioning are performable without the cable contacting itself.

4. The method of claim 1 and further comprising the step of:
fixing the location of the stop on the cable before passing the cable around the bone.

5. The method of claim 1 and further comprising the steps of:
after removing the tensioning tool from the cable, re-installing the tensioning tool on the cable;
operating the tensioning tool to establish the desired final tension in the cable;
crimping the stop onto the cable to hold the cable from slipping in the stop;
removing the cable clamp and the tensioning tool from the cable; and
cutting off the cable at the location where the cable clamp engaged the stop.

6. The method of claim 5 and further comprising the step of:
repeating steps of claim 1 on at least one other cable before the re-installing step of claim 3 on the first-mentioned cable.

7. The method of claim 5 and further comprising the step of:
including an implant device; and
passing the cable around the implant device before feeding the other end through the aperture in the stop.

8. The method of claim 5 and further comprising the steps of:
after re-installing the tensioning tool;
applying at least the same amount of tension on the cable in the tool as was established previously when the cable was previously tensioned; and
releasing from clamping relationship to the cable, a clamping member in the cable clamp.

9. A surgical cabling assembly comprising:
a crimp having an apertured crimpable portion;
a cable having an end portion fixed with respect to the crimp and an end portion receivable through the aperture in the crimp; and
a cable clamp having a lever-operated cam clamped to a portion of the cable which has been passed through the aperture in the crimp.

10. The cable assembly of claim 9 and wherein:
the clamp cam is arranged to tighten itself on the cable upon initiation of movement of the clamp along the cable in a direction away from the crimp.

11. The cable assembly of claim 10 and wherein:
the clamp cam is arranged to release itself sufficiently to accommodate movement of the clamp along the cable in a direction toward the crimp when the cable is pulled and the clamp is pushed by a tensioning tool.

12. The cable assembly of claim 11 and further comprising:
a tensioning tool having a passageway therein receiving a portion of the cable through it, the tool being clamped to the cable and having a portion thereof received in a socket in the cable clamp.

13. The cable assembly of claim 12 and wherein:
the tensioning tool has an elongate tip portion, with a tip thereon;
the cable clamp has a socket therein slidably receiving the tip portion of the tool, the socket having a bottom abuttingly engaged by the tip of the tool.

14. The cable assembly of claim 13 and wherein:
the cable clamp has an elongate tip portion having substantially the same maximum cross-sectional dimension as the tip portion of the tensioning tool.

15. The cable assembly of claim 14 and wherein:
the cable clamp tip portion and socket portion have generally cylindrical outer surfaces.

16. The cable assembly of claim 14 and wherein:
the cable clamp socket portion and tip portion are made of one homogeneous unit of cast metal.

17. Apparatus securing cables around bones and an implant in a spinal column and comprising:
a first cable having one end with a stop thereon, the cable adapted to encircle one bone and a part of an implant and extending through the stop to another end; and
a manually closable and releasable cable clamp means engaging the cable and the stop and holding tension in the cable for securing the cable to the bone and implant.

18. The apparatus of claim 17 and wherein the clamp means further comprises;
a clamp having a cam with lever operator thereon, the cam engaging the cable and locking the cable in the clamp, the lever being operable to release the cam from the cable when desired.

19. The apparatus of claim 17 and wherein:
the clamp means has a tool receiver means therein for reception of a cable tensioning tool.

20. The apparatus of claim 19 and wherein:
the tool receiver means is a socket fox reception of part of a tensioning tool therein.

21. The apparatus of claim 17 and further comprising:
a second cable having one end with a stop thereon, the second cable adapted to encircle another bone and a part of the implant and extending through the stop on the second cable to another end of the second cable; and
a second manually closable and releasable cable clamp means engaging the second cable and the stop on the second cable and holding tension in the second cable for securing the second cable to the second bone and the implant.

22. The apparatus of claim 21 and wherein the second clamp means further comprises;
a clamp having a cam with lever operator thereon, the cam engaging the second cable and locking the second cable in the clamp, the lever being operable to release the cam from the second cable when desired.

23. The apparatus of claim 21 and wherein:
the second clamp has a tool receiver means therein for reception of the cable tensioning tool.

24. The apparatus of claim 23 and wherein:
the tool receiver means in the second clamp means is a socket for reception of part of the tensioning tool therein.

* * * * *